United States Patent [19]

Knapp

[11] 3,963,770

[45] June 15, 1976

[54] SYNTHESIS OF ORTHO-CHLOROBENZALMALONONITRILE

[75] Inventor: John S. Knapp, Pittsburgh, Pa.

[73] Assignee: Federal Laboratories, Inc., Saltsburg, Pa.

[22] Filed: Aug. 12, 1974

[21] Appl. No.: 496,571

Related U.S. Application Data

[63] Continuation-in-part of Ser. No. 292,490, Sept. 27, 1972, abandoned.

[52] U.S. Cl. .............................................. 260/465 G
[51] Int. Cl.$^2$ ...................................... C07C 121/70
[58] Field of Search ................................ 260/465 G

[56] References Cited
UNITED STATES PATENTS

| | | | |
|---|---|---|---|
| 3,250,798 | 5/1966 | Shulgin | 260/465 |
| 3,715,379 | 2/1973 | Berry, Jr. et al. | 260/465 |

*Primary Examiner*—Lewis Gotts
*Assistant Examiner*—Dolph H. Torrence
*Attorney, Agent, or Firm*—Albert F. Kronman

[57] ABSTRACT

Disclosed herein is a synthesis of ortho chlorobenzalmalononitrile by reacting malononitrile with ortho-chloro benzaldehyde in methanol in the presence of a basic catalyst; separating the product crystals from the methanol; washing the crystals with fresh methanol; combining the wash methanol with the methanol filtrate and using the combined methanol in another similar synthesis run and repeating a series of such runs; drying the crystals with a current of turbulent dry air and scrubbing the air with base solution thereby substantially reducing associated problems of effluent treatment and ambient air pollution.

10 Claims, 1 Drawing Figure

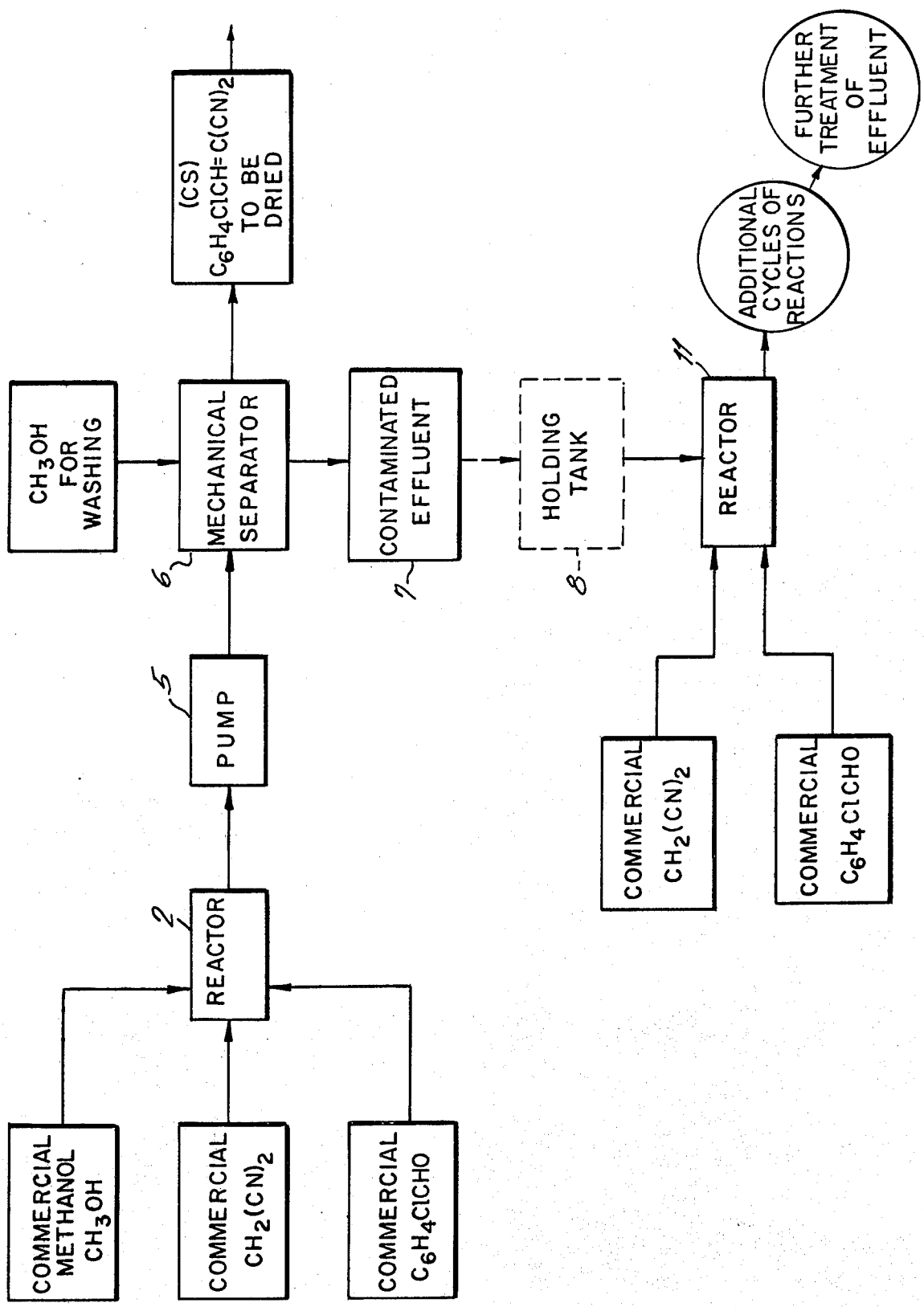

SYNTHESIS OF ORTHO-CHLOROBENZALMALONONITRILE

REFERENCE TO CO-PENDING APPLICATION

This application is a continuation-in-part of coassigned patent application Ser. No. 292,490, filed Sept. 27, 1972 and now abandoned.

SUMMARY OF THE INVENTION

The invention embodies an improved method for producing o-chlorobenzalmalononitrile, the improvement being that the process gives a good yield of a high-purity product while employing more economical equipment and/or producing less troublesome effluent than other processes used at present.

GENERAL DESCRIPTION

The lachrymating agent o-chlorobenzalmalononitrile, (hereinafter referred to as CS, which is the U.S. Army Chemical Corps. designation also widely used by the riot control community), has gained wide-spread acceptance as a riot control agent by the U.S. Army and many civil police forces. CS has been characterized as having a low toxicity and a high irritant potency compared to other common riot control agents (see "Special Summary Report on the Toxicology of CN, CS, and DM" Directorate of Medical Research; Chemical Research and Development Laboratories; U.S. Army Edgewood Arsenal; Edgewood, Md.). Large quantities of CS in various physical forms and mixtures have been employed throughout the Free World for both riot control and military purposes. However, since CS is extremely irritating, its synthesis entails formidable problems of air and water pollution. These problems have been intensified by the requirement on the operator of the process to meet more and more stringent rules by various governmental agencies regulating the quality of effluents released to the environment. A further consideration is the need to find economically feasible means to treat the process effluent in order to bring it into compliance with environmental quality standards and yet not increase excessively the cost of the produced CS. It is a purpose of this invention to alleviate these problems of air and water pollution.

In at least one process that has been used to synthesize large quantities of CS, several factors militate against realizing the above requirements to a practical extent. Among these factors are the relatively large volume of contaminated effluent produced, and the inadequacy of routinely practiced decontamination methods in the face of tightened effluent quality regulations. In the synthesis just referred to, equimolar quantities of o-chlorobenzaldehyde and malononitrile, with or without the presence of a base catalyst, and dissolved in a mixture of alcohol and water, react to form CS and water:

military and commercial use must meet rather rigorous requirements for purity, melting point range, and residual impurity limits, as typified by the requirements of U.S. Government military specification MIL-C-51029 (CmlC). In the synthesis process, various solvents and solvent mixtures have been proposed, such as ethanol, isopropanol, or a mixture of either of these with water (see "Process laboratory study of the preparation of CS(U)", CWL Technical Memorandum 31–83, U.S. Army Chemical Warfare Laboratories, Army Chemical Center, Maryland, July 30, 1959). In a typical process approximately 1800 gallons of contaminated effluent are generated for each ton of dry CS synthesized. This effluent contains significant amounts of CS in solution and suspension, and various residual compounds from the reaction. Treatment of this effluent by the decontamination method suggested by governmental procuring agencies, that is by mixing the effluent with caustic soda, lime, or other basic material, has not proved satisfactory, in that while such treatment can hydrolyze the CS to form less irritating compounds, the biochemical oxygen demand (BOD) and chemical oxygen demand (COD) of the resulting effluent remain high, and the (—CN) radical is not decomposed by this treatment. Each of these factors must be substantially reduced by further treatment before the effluent quality comes into compliance with the standards of various environmental regulations.

STATE OF THE ART

The art to which this invention relates already is aware of U.s. Pat. Nos. 3,250,798 and 3,715,379. The first of these alleges no advantage for the use of methanol, does not reuse its solvent, nor seeks to avoid pollution problems. The second describes a solventless synthesis which is believed to produce low yields. That process also requires a carbon dioxide purge, use of a heavy stirrer drive and of a closed vessel.

GENERAL DESCRIPTION

Some objects of the present invention are to achieve a process for the synthesis of CS, in relatively simple process equipment, under mild conditions of temperature and pressure, with a substantial reduction in volume of effluent, the effluent being of a character that makes it amenable to virtually complete conversion to non-noxious material. The achievement of these objects is possible by employing 100% commercial grade methanol (e.g.E.I. DuPont methanol) as the reaction solvent, and reusing the solvent recovered from one run as the solvent for another run, and so on for a number of runs. A significant saving in methanol used in the process is thus realized. Additional methanol used to wash the recovered crystals of CS is added to the main body of reaction solvent to make up for various solvent losses. Any CS dissolved by this washing is not lost but merely carried along, helping to saturate

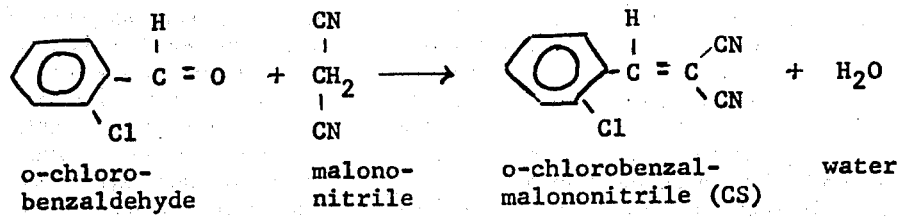

o-chloro-benzaldehyde + malono-nitrile → o-chlorobenzal-malononitrile (CS) + water The CS is then extracted and washed with an additional quantity of alcohol and water. Most CS prepared for the added methanol, which saturation has the desirable effect of increasing the percentage of CS recovered. It will be apparent to those versed in the art that the CS formed by this process will dry more readily, as for example, with a lower heat input, than CS formed in the methanol-water mix mentioned previously, since methanol possesses a substantially higher volatility than water. In a series of CS runs made in this manner, CS from as late as the 16th run in the series was within the limits of purity, melting point range, and percent residuals set forth in specification MIL-C-51029 (CmlC). Drying with hot air is facilated by first centrifuging the crystals. When at the end of a series of runs the methanol has come to contain such a quantity of impurities that the quality of the CS produced is impaired, the methanol may be destroyed by burning in at least one type of high-efficiency incinerator, or recovered by distillation and further reused. Since the methanol is itself flammable, economy is realized by the need for little or no added fuel to assist in the pyrolytic destruction of the methanol. Alternatively, the relatively high volatility of the methanol would make it readily distillable for purification and reuse.

Reference is made to the accompanying drawing which forms a part hereof and consists of a block flow diagram of a batch process for the manufacture of CS.

As shown in the diagram, a manufacture flow sheet according to a preferred embodiment of the invention involves the following steps:

Step I. A measured quantity of commercial grade methanol ($CH_3OH$) is added to a temperature controllable, hooded, cylindrical, non-rusting reactor 2 provided with a stirrer. To this in turn are added a measured quantity of commercial grade malononitrile ($CH_2(CN)_2$) a small quantity of a basic catalyst such as piperidine, triethanolamine, or triethylamine and commercial grade o-chlorobenzaldehyde ($C_6H_4CLCHO$). Substantially stoichiometric amounts of the reactants are used.

The contents of the reactor are stirred for a predetermined time at a predetermined temperature to permit the reaction to run essentially to completion, forming CS ($C_6H_4ClCHC(CN)_2$).

Step II. Upon the completion of Step I, the contents of the reactor 2 are transferred by pump 5, or by gravity or other means of conveyance, to a mechanical separator such as a centrifuge 6.

Step III. The reaction solvent, containing dissolved and suspended matter from the CS synthesis reaction is conducted from the mechanical separator 6 to holding tank 8 until the appropriate time to use it as reaction solvent for another synthesis run. If a second reactor 11, similar to reactor 2 is available, the reaction solvent may be conducted directly to it, and holding tank 8 becomes unnecessary to the process. For this reason holding tank 8 is indicated by a dashed-line block.

Step IV. The crystalline cake retained in the mechanical separator 6 may be further purified by washing with an additional portion or portions of fresh commercial methanol. These washings are conducted to and combined with the reaction solvent as described in Step III. The volume of this fresh solvent may be adjusted to approximately replace the amount of solvent lost by evaporation, entrapment, and other loss-producing effects.

Step V. The washed crystalline CS is removed from the mechanical separator 6 and subjected to an appropriate drying process to render it fit for its intended use. The crystalline CS, being moist almost solely with methanol, will dry more readily than if moist with a mixture of methanol and water as in certain other CS synthesis methods.

Step VI. To the combined reaction solvent and washing solvent from Step III, residing either in a second reactor 11, or in reactor 2 after being emptied of the previous run, are added measured quantities of commercial grade malononitrile, piperidine and o-chlorobenzaldehyde, and the synthesis process is repeated as in Step I. This same cycle of steps (Steps I–VI) is repeated until the reaction solvent will no longer yield acceptable CS.

Step VII. The no longer useable reaction solvent from the repeated cycles described in Step VI can be destroyed by proper incineration or otherwise disposed of consistant with applicable government regulations, or distilled to recover the methanol for further reuse.

The following examples are presented as illustrative of the invention for a better understanding.

EXAMPLE I

115 Grams of commercial grade malononitrile and 250 grams of commercial grade o-chlorobenzaldehyde were added to 890 grams of commercial grade methanol. The solution was heated gently and stirred. 0.4 Grams of piperidine was added. The temperature reached a maximum of 53°C. Stirring was continued for 1 hour. The resultant CS crystals were recovered by filtration in a Buchner funnel on Whatman No. 30 filter paper with vacuum. The crystals were washed with fresh methanol and the washings were added to the main volume of filtrate. 890 Grams of the filtrate from Run No. 1 were used as the reaction solvent for another run, using the same amounts of o-chlorobenzaldehyde and malononitrile as in Run No. 1. This process was repeated until six batches of CS designated as Run Nos. 2 to 6 inclusive, had been synthesized. A small amount of piperdine was needed to catalyze the later runs. The analytical results from the first and last run of the series are shown in Table 1, below:

TABLE I

|  | Assay, % | MP,°C | % Residuals |
|---|---|---|---|
| Limits, MIL-C-51029* | 96.0 min. | 93.0–96.5 | ≤1.0 |
| Run No. 1 | 97.0 | 95.2–95.6 | <<1.0 |
| Run No. 6 | 96.4 | 95.2–95.6 | <<1.0 |

*The % Assay was determined by the wet method, using the Volhard titration; the % REsiduals was determined by gas-liquid chromatography; both per various rvisions of MIL-C-51029 (CM1C).

EXAMPLE II

345 Grams of malononitrile were added to 2670 grams of methanol, both commercial grade. This solution was warmed to 35°C. 750 Grams of commercial grade p-chlorobenzaldehyde and 0.4 grams of piperidine were added and the solution was stirred for 30 minutes. Maximum temperature reached was 50°C. The solution was then cooled to 32°C and filtered. The retained CS crystals were washed with 185 grams of fresh methanol. This methanol was added to the main volume of filtrate. This combined filtrate was used as the reaction solvent for another similar run, and so on for a series of sixteen batches of CS. The cumulative average yield for the 16 runs was 96.5% of theoretical. In the pertinent laboratory records, the runs were numbered 1–16. All CS thus made met the requirements of specification MIL-C-51029 (CMIC). Results from several of these runs are shown in Table II, Below:

TABLE II

| | Assay, % | MP, °C | Residuals |
|---|---|---|---|
| Limits, MIL-C-51029* | 96.0 min. | 93.0–96.5 | ≤1.0 |
| Run No. 5 | 96.0 | 94.6–95.0 | <<1.0 |
| Run No. 11 | 97.0 | 94.9–95.2 | <<1.0 |
| Run No. 16 | 97.4 | 94.8–95.1 | <<1.0 |

*The % Assay was determined by the wet method, using the Volhard titration; the % Residuals was determined by gas-liquid chramatography; both per various revisions of MIL-C-51029 (CmlC).

A portion of wash methanol was incinerated by spraying through the flame of an incineration burner. No fumes of CS or other irritating compounds were detected in the incinerator discharge air. A portion of methanol was distilled in laboratory glassware. A single distillation rendered it suitable for re-use as solvent for CS synthesis.

EXAMPLE III 92 lbs. of melted malononitrile was added to 711 lbs of methanol in an open, jacketed 250 gal. reactor equipped with an anchor stirrer. The mixture was brought to a temperature of 37°C. Four ounces of piperidine were added, followed by 200 lbs. of o-chlorobenzaldehyde at a temperature of approximately 35°C. The mixture was stirred without further heating. The temperature of the batch reached a maximum of 54°C. approximately one-half hour after the beginning of the reaction. The stirrer was allowed to run for a quarter of an hour, and then the reactor was cooled. The reactor was unloaded when the mix temperature was 35°C. The resulting slurry was run through a centrifugal wringer, the liquor being directed to a waiting reactor similar to the first one. The cake of CS crystals in the wringer was washed with two 10 gallon portions of methanol, which were added to the liquor in the second reactor. This liquor was then used to synthesize another batch of CS. The conditions were essentially the same as described above except that 94 lbs of malononitrile were used instead of 92 lbs. After this second batch of CS was synthesized, these steps were again repeated to produce a total of four batches of CS. The wash methanol added after each synthesis did not increase the volume of liquid unduly because some methanol was lost by evaporation during the reaction.

The CS produced was dried in a "Jet-O-Mizer" fluid jet dryer by a turbulent current of warm air. The effluent air from the dryer was satisfactorily freed from CS and CS fumes by a packed scrubbing tower in which a solution of 10–30% sodium hydroxide was circulated.

The CS produced in the above series of reactions was of good quality. It contained well under 0.2% each of residual malononitrile and o-chlorobenzaldehyde. The melting point range of the material was approximately 95.2–95.8°C.

What is claimed is:

1. A batch process for the synthesis of ortho-chlorobenzalmalononitrile, comprising, the steps of:
   a. mixing in methanol malononitrile with o-chlorobenzaldehyde in the presence of a catalytic amount of a basic amine catalyst;
   b. heating the resulting solution to 35° to 55°C;
   c. physically separating the resulting product crystals from said methanol;
   d. washing the product crystals with fresh methanol;
   e. combining the resulting methanol washings with said methanol filtrate;
   f. reusing the combined methanol in another similar series of steps $a - e$ as above defined;
   g. and repeating a batch series of such synthesis until said methanol contains an excessive amount of impurities; whereby less volume of methanol solvent is used overall and associated problems of effluent treatment and air pollution are minimized.

2. The process of claim 1, wherein said crystals are separated by centrifuging.

3. The process of claim 1, wherein said crystals are separated by filtration.

4. The process of claim 1, wherein said methanol solvent containing excessive impurities is distilled to remove such impurities and recycled.

5. The process of claim 1, wherein said methanol solvent containing impurities is incinerated to dispose of same.

6. The process of claim 1, comprising first heating to around 35°C, a mixture of methanol and malononitrile, then adding o-chlorobenzaldehyde and piperidine and stirring, allowing the temperature to rise to about 50°C and cooling to about 32°C.

7. The process of claim 1, wherein said catalyst is piperidine, triethylamine or triethanolamine.

8. The process of claim 1, further comprising the steps of drying said crystals by passing a current of turbulent dry air thereover.

9. The process of claim 8, wherein said air is scrubbed with an aqueous alkali solution after passage over said crystals.

10. The process of claim 9, wherein said solution is aqueous sodium hydroxide.

* * * * *